United States Patent [19]
Wong et al.

[11] Patent Number: 5,825,031
[45] Date of Patent: Oct. 20, 1998

[54] TOMOGRAPHIC PET CAMERA WITH ADJUSTABLE DIAMETER DETECTOR RING

[75] Inventors: Wai-Hoi Wong; Jorge Uribe, both of Houston, Tex.

[73] Assignee: Board of Regents The University of Texas System, Austin, Tex.

[21] Appl. No.: 730,036

[22] Filed: Oct. 11, 1996

[51] Int. Cl.$^6$ ................................................ G01T 1/164
[52] U.S. Cl. ........................................... 250/363.03
[58] Field of Search ................ 250/363.02, 363.03, 250/363.04

[56] References Cited

U.S. PATENT DOCUMENTS

| | | |
|---|---|---|
| H12 | 1/1986 | Bennett et al. ............... 250/363.03 X |
| 4,259,578 | 3/1981 | Thompson . |
| 4,368,389 | 1/1983 | Blum . |
| 4,473,749 | 9/1984 | Derenzo et al. . |
| 4,755,680 | 7/1988 | Logan . |
| 4,980,552 | 12/1990 | Cho et al. . |
| 5,039,859 | 8/1991 | Sanz et al. . |
| 5,075,554 | 12/1991 | Yunker et al. . |
| 5,197,088 | 3/1993 | Vincent et al. . |
| 5,206,512 | 4/1993 | Iwao . |
| 5,319,204 | 6/1994 | Wong . |
| 5,451,789 | 9/1995 | Wong et al. . |
| 5,453,623 | 9/1995 | Wong et al. . |

FOREIGN PATENT DOCUMENTS

| | | | |
|---|---|---|---|
| 62-207986 | 9/1987 | Japan ................................ | 250/363.03 |

OTHER PUBLICATIONS

Townsend et al., "A Rotating PET Camera Using BGO Block Detectors," *1991 IEEE Nuclear Science Symposium Conference Record*, 1658–1662, 1991.

Wong et al., "A 2–Dimensional Detector Decoding Study on BGO Arrays with Quadrant Sharing Photomultipliers," *IEEE Trans Nuclear Science*, 41(4):1453–1457, Aug. 1994.

Wong et al., "An Analog Decoding BGO Block Detector Using Circular Photomultipliers," *IEEE Trans Nuclear Science*, 42(4):1095–1101, Aug. 1995.

Wong et al., "Design of a Variable Field Prototype Pet Camera", presented in the 1995 Nuclear Science Symposium of the Institute of Electrical and Electronic Engineers (IEEE).

Wong, "A Positron Camera Detector Design with Cross–Coupled Scintillators and Quadrant Sharing Photomultipliers,"*IEEE Trans Nuclear Science*, 40(4):962–966, Aug. 1993.

*Primary Examiner*—Edward J. Glick
*Attorney, Agent, or Firm*—Arnold, White & Durkee

[57] ABSTRACT

A PET camera is disclosed with radially translating detector segments coupled with a rotational motion to tailor the camera detector ring to the size of the subject for optimal detection efficiency. In particular methods of using the present invention, the detector segments may be radially translated to describe a small diameter in imaging a small object, such as a breast. Alternately, the detectors may comprise a large diameter to image a large object, such as body. The detector segments may be diametrically opposed for optimal positron detection. The present invention may be coupled with a quadrant-sharing-photomultiplier-detector design.

17 Claims, 19 Drawing Sheets

TOMOGRAPHIC PET CAMERA WITH ADJUSTABLE DIAMETER DETECTOR RING

This invention was made with government support under contract nos. NIH-RO1-CA58980 and NIH-CA5 898002S1 awarded by NIH. The government has certain rights in this invention.

FIELD OF THE INVENTION

The present invention relates to gamma or positron emission tomography (PET) cameras.

BACKGROUND OF THE INVENTION

A PET camera typically consists of a polygonal or circular ring of radiation detection sensors placed around a patient area. Radiation detection begins by injecting certain isotopes (radionuclides) with short half-lives into a patient's body placeable within a patient area. The isotopes are absorbed by target areas within the body causing the isotope to emit positrons that are detected when they generate gamma rays. When in the human body, the positrons collide with electrons and the two annihilate each other, releasing gamma rays. The emitted rays move in opposite directions, leave the body and strike the ring of radiation detectors, thereby indicating areas of concentration of the injected isotopes.

The heart of a PET camera is a detection system made up of many large detector rings, each with hundreds or thousands of small radiation detectors surrounding the patient. The detection system detects the pairs of gamma-rays emitted by the positron tracers injected into a patient or subject. Examples of detection systems that may be used with the present invention are shown in U.S. Pat. Nos. 5,319,204 and 5,453,623, both of which are hereby incorporated by reference. Each small detector is served by a complex network of circuits to process the signal from the detectors and the processed signal is sent to a computer for data storage and image display.

PET cameras may be used, for example, in the areas of neurology (localizing the sites of long and short term memories, mathematical skill, subjective and objective processes, different brain functions between men and women, etc.), cardiology, and oncology. In oncology, potential applications are in whole body tumor/metastases localization, treatment response monitoring, differentiation of recurrence from necrosis, tumor estrogen receptor density imaging, quantitative imaging of tumor glycolysis rate, tumor protein synthesis rates, and DNA synthesis rates. In particular, PET cameras may be used to detect the presence of malignant cells in a patient. For example, a PET camera may be used to test a woman for malignant breast cells. PET testing is preferred over X-ray mammography, which images tissue density differences. X-ray mammography is relatively ineffective for younger women, as normal breast tissue in these women has nearly the same density as cancer. Further, differentiating benign from malignant lesions is difficult in mammograms. PET testing, however, is capable of detecting the higher metabolic rates associated with the higher proliferation rates characteristic of malignant cells compared to normal cells. A further advantage of PET testing is the specificity of PET screening results, as about 80% of the masses detected by X-ray mammography are false positives. These false positives therefore require unnecessary biopsies.

There are several drawbacks to using typical PET camera systems. First, typical PET cameras are whole body imaging devices, which are extremely expensive (approximately $2.5 million), and have high maintenance costs (approximately $250,000/yr.). These devices can image any part of the body, but the detection efficiency and image resolution is lower for imaging small objects, such as the brain, breast, limb and animal models. For imaging the breast, the detection efficiency is even lower, because the chest has to be included in the imaging field, and the chest absorbs the majority of the positron signal.

The high cost of PET is one reason for its slow growth in the marketplace. Another reason for its slow reception is that its image resolution needs to be improved further, especially for small animal research and neurological applications. The present invention seeks to correct these and other drawbacks.

A conventional PET camera may cost approximately $2,700,000. Recently, Siemens Corporation, in an attempt to lower the PET camera cost, introduced a camera which eliminates approximately ⅔ of the detector sectors/segments as shown in FIG. 1. The remaining detector segments 2 rotate 180° around a patient to cover for the missing detectors, as shown in FIG. 1. This new camera costs approximately $1–1.4 million. However, the rotating camera has drawbacks. The positron signal is a pair of gamma-rays 4 emitted back-to-back from each other, as seen in FIG. 1. Thus, the camera of FIG. 1 has a large acceptance-angle for the positron-gamma-pair from the center, but zero tolerance (detection sensitivity) for points near the edges of the detector segment. Therefore, the image quality and resolution are good at the center, but worsen as distance from the center increases. Also, for small subjects and organs, the missing detectors cause a significant loss in detection efficiency because of the large detection gaps and the large distance between the small subject and the remaining detectors. Further, to compensate for the missing detectors, the two detector segment design rotates a large angle of 180° for complete data acquisition. This rotation takes more time. If the dynamics of the testing isotopes are fast changing, such as in the imaging of neurological activation sites, larger angular rotation produces more imaging artifacts (shooting at a moving target). Therefore, the PET camera of FIG. 1 may not attain desired performance and quantitative accuracy. Furthermore, a large angular rotation requires complex "slip-ring" technology to provide electrical and signal transport between the fixed and moving parts of the gantry.

Thus a need exists for a PET camera that is relatively inexpensive in comparison to prior art systems, yet still capable of high resolution imaging. Additionally, a need exists for a PET camera capable of high resolution imaging of small objects.

SUMMARY OF THE INVENTION

The present invention includes a PET camera for imaging objects. The camera includes a plurality of position sensitive radiation detectors capable of radial translation with respect to a central axis. The plurality of position sensitive radiation detectors are arranged in arcuate relation to each other and adapted to surround an object to be imaged.

The present invention also includes a radiation shield system for a PET camera, comprising a pair of radiation shields, which may surround each of a plurality of detector heads, and a plurality of supplemental radiation shields, which may be fixed around a rotating plate of a gantry on which each of the plurality of detector heads are mounted. Each of the plurality of supplemental radiation shields may be adjacent to one of the plurality of detector heads. Additionally, a plurality of removable supplemental shields may be removably attached to a fixed plate of the gantry.

The present invention also includes a method of testing a patient for breast cancer, comprising the steps of obtaining an apparatus according to the present invention; placing a gantry containing the apparatus in a horizontal or tilted position; injecting the patient with radioactive isotopes; placing the patient in a substantially prostrate orientation, thereby placing a breast of the patient within the plurality of position sensitive radiation detectors; adjusting the plurality of position sensitive radiation detectors, thereby placing the plurality of position sensitive radiation detectors within close proximity to the breast; and imaging the breast using the plurality of position sensitive radiation detectors.

DETAILED DESCRIPTION OF EXEMPLARY EMBODIMENTS

Figure 1:
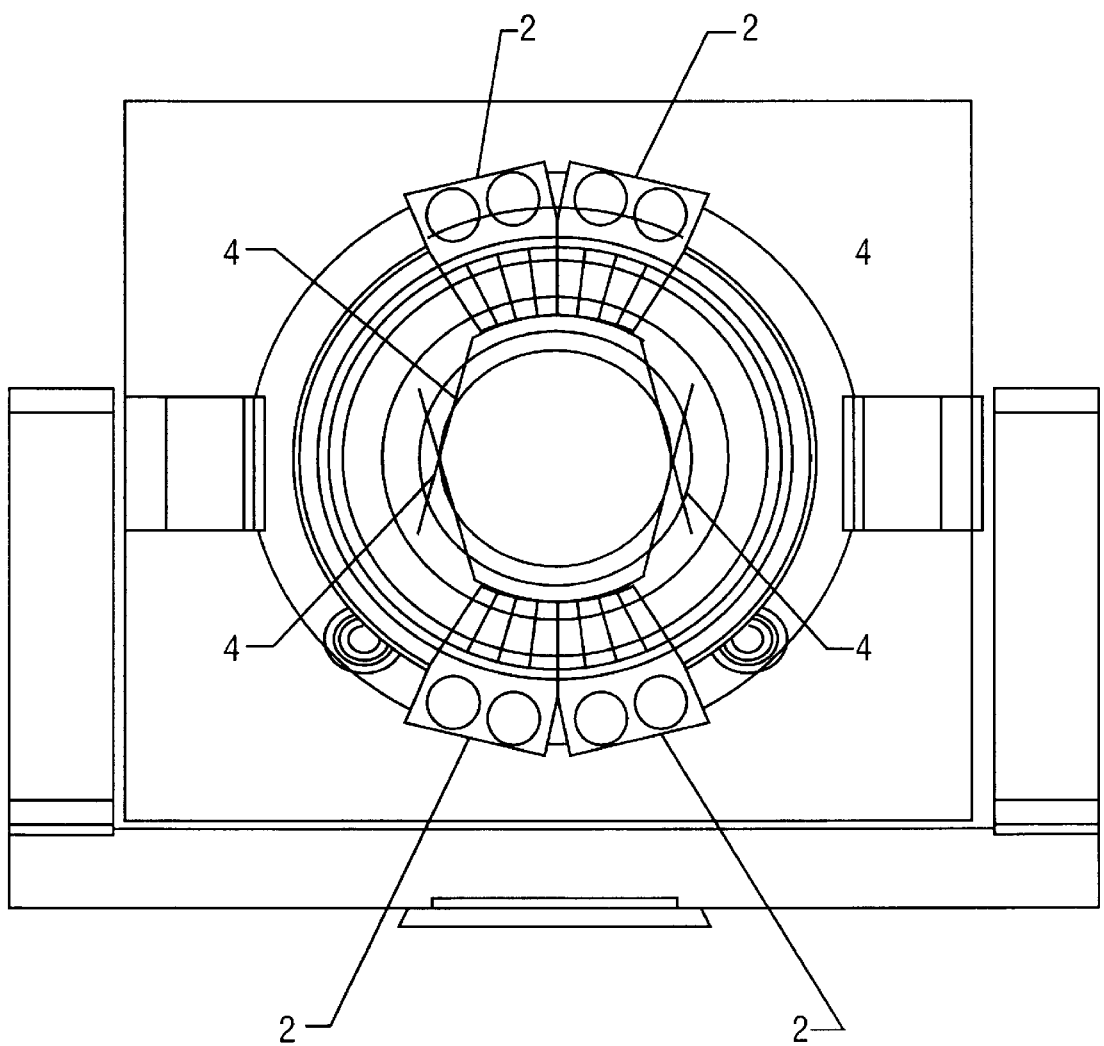
FIG. 1 is a diagram of a PET camera known in the prior art having only top and bottom detector segments.
Figure 2A:
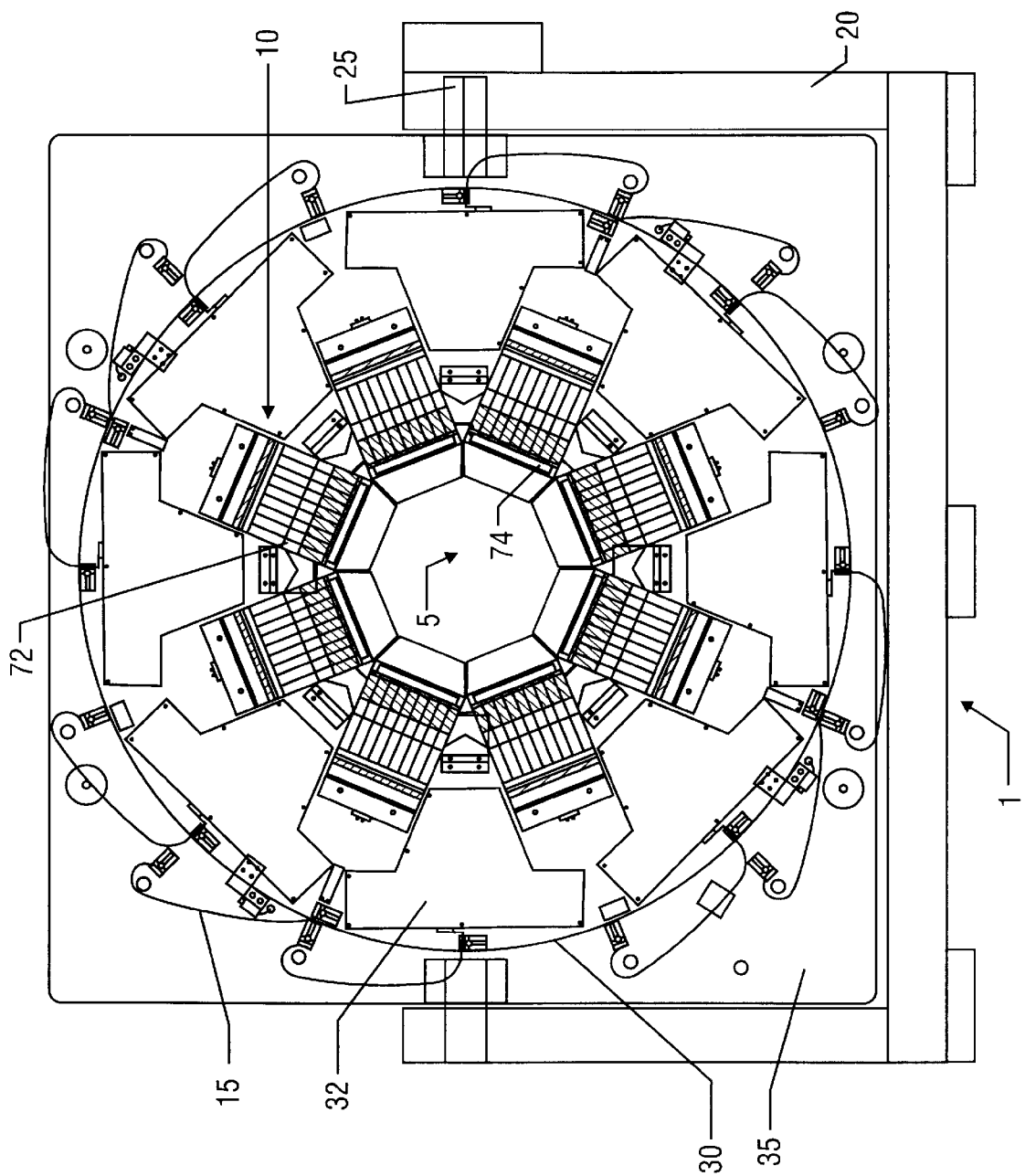
FIG. 2A is a diagram of a PET camera according to the present invention.

A design goal of the present invention is a lower cost, high resolution camera with some sensitivity sacrificed for whole body imaging, but with higher sensitivity for small object imaging (brain, breast and small animals). A diagram of the PET camera of the present invention is shown in FIG. 2A. This new camera 1 may be comprised of, for example, eight individual detectors which may be referred to as segments or detector heads 10. These detector heads 10 may be translated radially with respect to a central axis. Each detector head 10 may have, for example, between 8 and 100 photomultiplier tubes (PMT's) 72. In an exemplary embodiment, each detector head 10 may have 27 PMT's 72. Additionally, each detector head 10 may have, for example, between 3 and 81 blocks (not shown). In an exemplary embodiment, each detector head 10 may have 16 blocks. Further, each block may include a plurality of scintillation crystals 74. Each block may have between 36 and 256 crystals, and an exemplary embodiment may have 49 crystals 74. The PMT used may be, for example, the Philips 1911 PMT (19 mm diameter), or a Hamamatson 1548. Instead of PMT's and scintillation crystals, the present invention may use scintillation crystals and solid-state optical sensors. Furthermore, detector heads used in the present invention may use Siemens CTI detector design, the GE/Quest, or the GE/Advantage detector design or other position sensitive detector designs.

FIG. 2A shows a block diagram of a PET camera 1 according to the present invention. FIG. 2A shows a plurality of detector heads 10 which are arranged around an area 5 in which an object to be tested may be placed. The detector heads 10 may be placed on a rotating plate 30, which is attached to a fixed support plate 35. The fixed support plate 35 may be attached to support stand 20, which has pivot 25. Pivot 25 permits the entire camera 1 to be tilted horizontally so that a patient may lie prone on the PET camera 1 for more accurate testing of particular body parts; for example, breast imaging.

The detector heads 10 may be closely packed into an approximately 30–50 cm diameter detector ring in the smallest field-of-view mode. This mode is especially useful in testing, for example, breast tissue. In this mode, the PET camera has higher detection sensitivity than the typical 80 cm detector ring of commercial cameras. The sensitivity gain in this embodiment is approximately 2× for brain and 10× for breast. This high sensitivity mode may be useful for brain, breast and animal imaging.

Figure 2B:
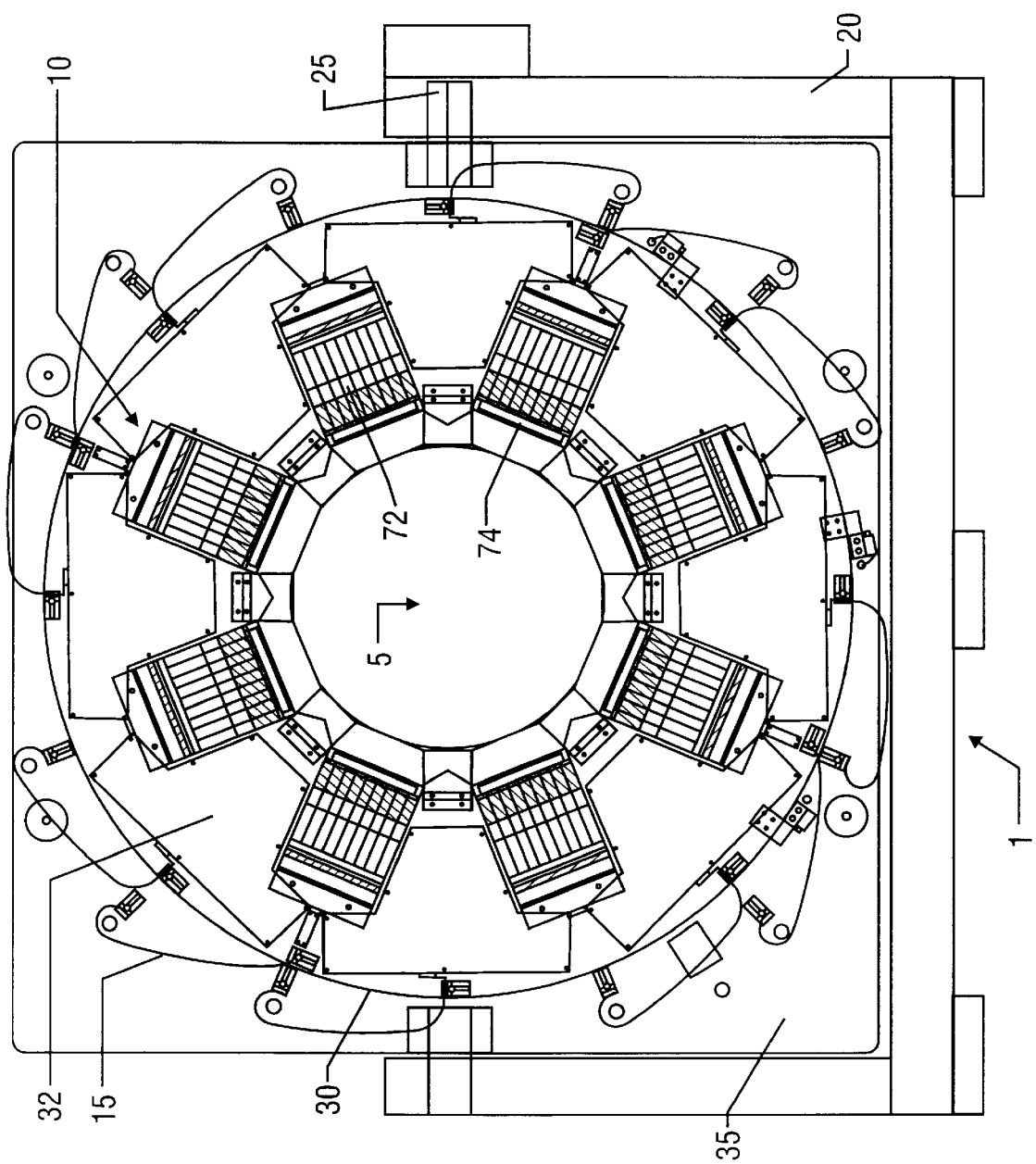
FIG. 2B is a diagram of a PET camera according to the present invention.

For imaging the body, the detector heads 10 may be radially displaced to a larger diameter, as shown in FIG. 2B. The maximum detector ring diameter for this design may be approximately 55–90 cm. The relative sensitivity compared to a regular whole body camera (no detector gap) with an 80 cm diameter ring and similar axial-FOV is approximately 0.4. Hence, the camera gains approximately 100% in sensitivity for imaging brain, breast, limbs and animals, but loses approximately 60% in sensitivity in whole body imaging, while saving approximately 40% in detection system and electronics cost.

Figure 3A:
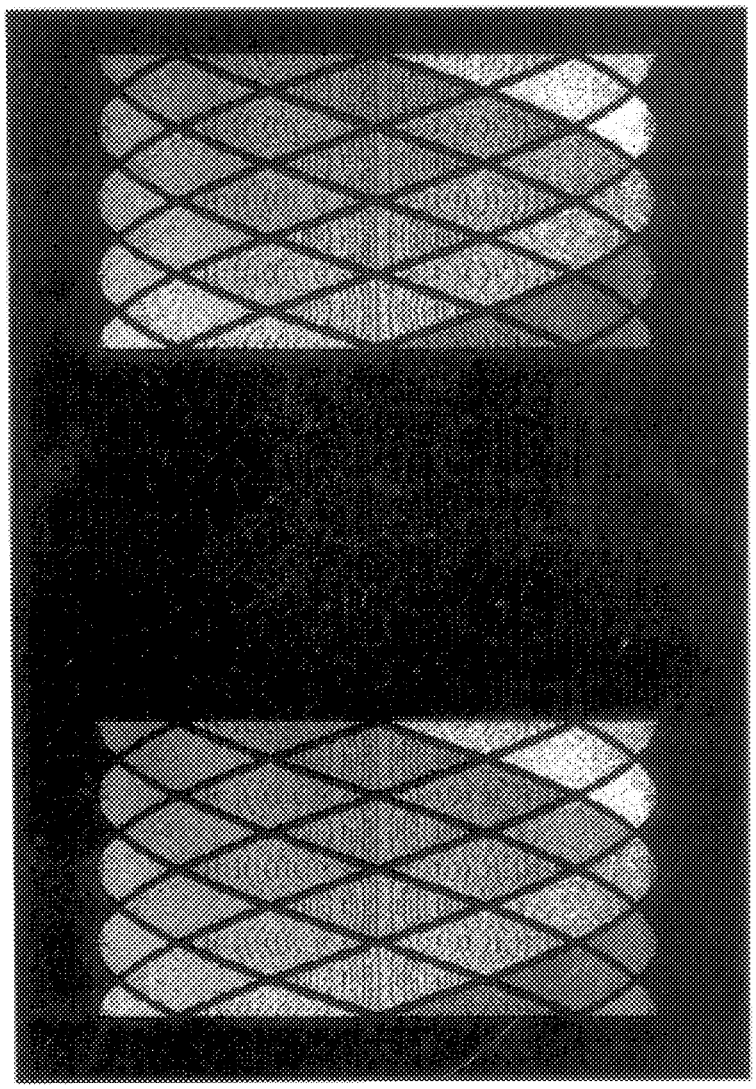
FIG. 3A is an illustration of a sinogram showing the data sampling of a PET camera according to the present invention having a small field-of-view.
Figure 3B:
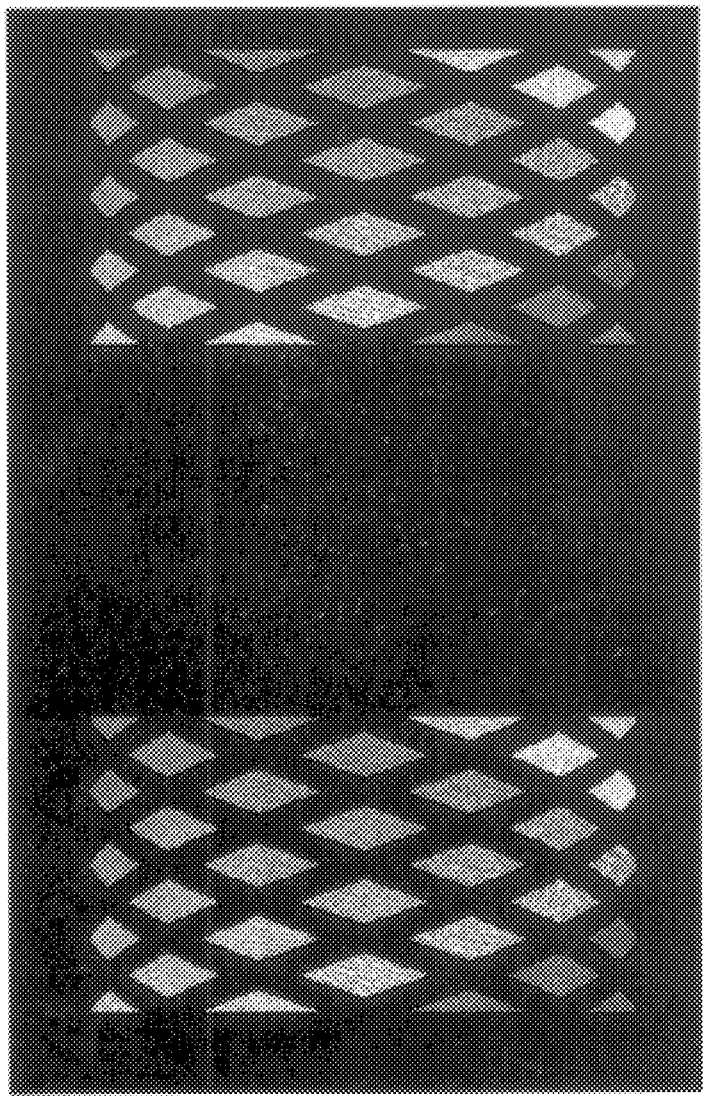
FIG. 3B is an illustration of a sinogram showing the data sampling of a PET camera according to the present invention having a larger field-of-view.

For the larger field-of-view mode of operation, the camera may be rotated up to approximately 45° to sample sinogram data missed at the gaps. An exemplary sinogram is shown in FIG. 3B. As shown in FIG. 2A, the detector heads 10 may be mounted on rotating plate 30, controlled by a servo-motor (not shown). Also as shown in FIG. 2A, all of the front end electronics 32 of the camera may be placed on the rotating plate 30 (between the detector gaps) to maximize signal-to-noise ratio and space utilization. The detector heads 10 may be connected to the front end electronics 32 by means of flexible ribbon cables 15, for example. The only electronics outside the camera are coincidence circuits (not shown) and a data acquisition computer (not shown), which may occupy, for example, half of a 19" VME rack (not shown). The data acquisition computer may be, for example, a single board 68040 CPU with 64 MB RAM (using OS-9 real-time operation system) with an Ironics Data Transporter board, which controls the camera rotation and is capable of binning the detector addresses into sinograms at a sustained rate of 250K events/second (software binning). Other data acquisition computer configurations, such as a Power PC with a VME/PMC Bus may also be used.

Figure 2C:
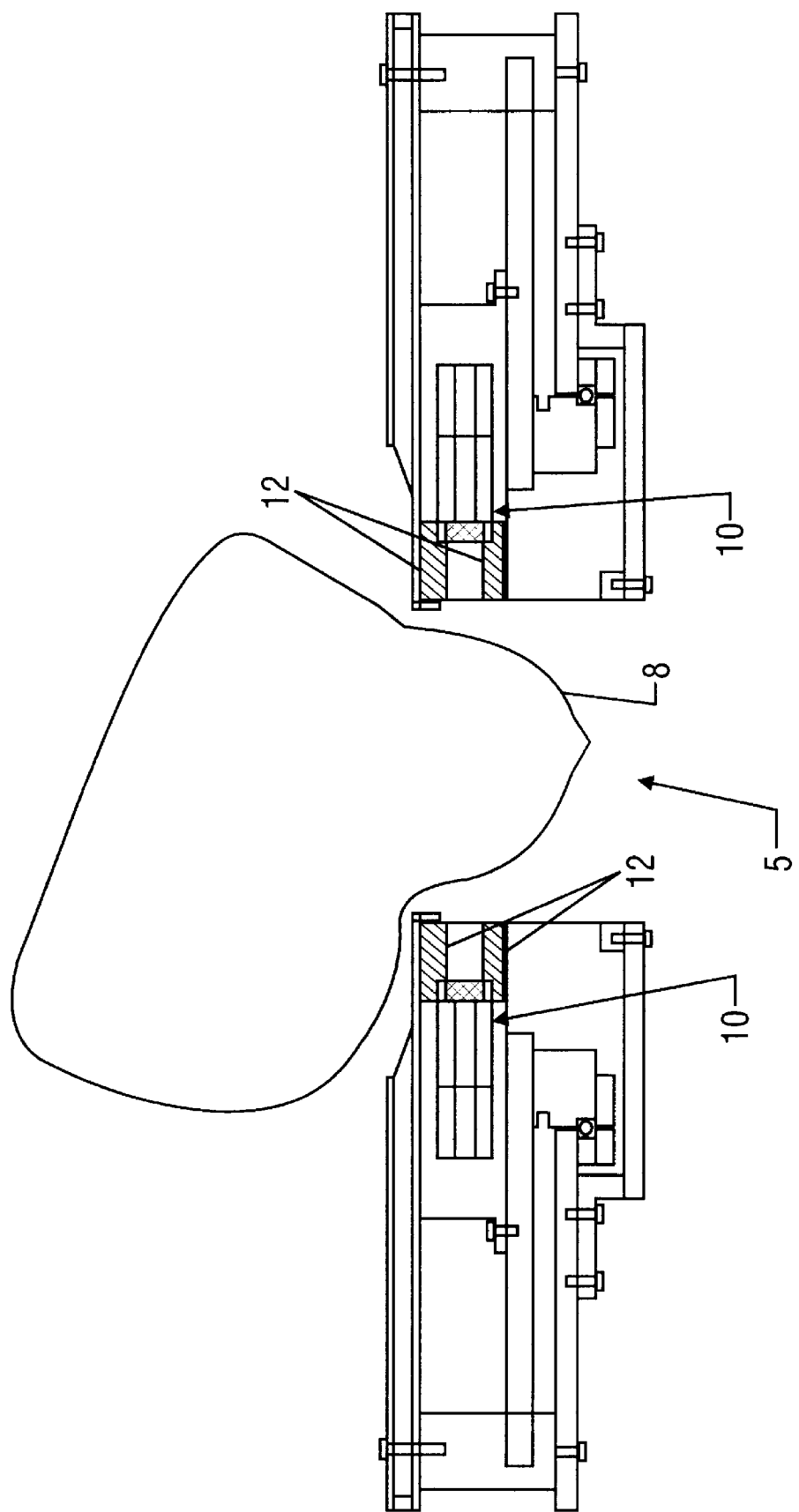
FIG. 2C is a cross-sectional diagram of a PET camera according to the present invention.

The camera may be tilted horizontally to image a single breast with the patient in the prone-position on the camera, allowing the maximum amount of breast tissue 8 to be imaged, as shown in FIG. 2C. To minimize the amount of tissue near the chest wall which cannot be imaged, depleted uranium shielding 12 may be used around the exterior of the detector head 10, since the half-value-thickness of $^{238}$U is half that of lead for 511 KeV gamma. This embodiment may be beneficial for finding early or small breast tumors, since the attenuation of the gamma-pair by the body is avoided (this absorption is between 70–90%). Multiplying this effective sensitivity gain (4×) by the 1.8× gain in sensitivity due to the small ring geometry provides a 7 times sensitivity gain compared to the regular imaging geometry with the whole patient body laying supine inside a large detector diameter. Coupling the large detection sensitivity gain to a very high resolution detection system (for example, 2.6×2.6 mm BGO) using a photomultiplier-quadrant sharing design, as disclosed in U.S. Pat. No. 5,319,204, which is hereby incorporated by reference, very small primary breast tumors may be detected.

As discussed above, exemplary embodiments of the present invention are shown in FIGS. 2A–2C. Radial translation of the detector heads 10 permits small objects, such as a human head, breast or small animals to be imaged, with the detector heads 10 forming a complete detector ring, as shown in FIG. 2A. Therefore, rotation may not be necessary because there are fewer missing detectors. Further, because there are fewer missing detectors, detection efficiency/sensitivity does not suffer, and the small detector ring is closer to the object so that the detection sensitivity is significantly improved over that of the regular conventional PET (camera with a full ring). The elimination of rotation implies that fast dynamic imaging (mostly for brain imaging) may be performed with fewer imaging errors.

For imaging large objects or whole body imaging, the detector segments may be pulled out radially, as shown in FIG. 2B, to accommodate the larger size. In this larger detector-ring configuration position, the camera has gaps (missing detectors), and rotation may be needed to cover the gaps. Because the gaps may occur approximately every 45° in the eight-segment design as shown in FIG. 2B, only a 45° rotation may be required, which is much smaller than the 180° rotation of the prior art. For an n-segment design, the total rotation angle is approximately 360°/n. Hence, the rotating data acquisition may be accomplished faster with 450° or 360°/n (for n>2) rotation, and imaging errors in the imaging of dynamic/studies (time-activity imaging) such as those used for physiological modeling or parametric imaging are also lower. Furthermore, since the gaps may be more evenly distributed over the whole ring (instead of the two large gaps of the prior art), the uniformity in detection sensitivity in the present invention is higher. In other words, the sensitivity does not go from a maximum at the camera center to zero at the edges of the detector segment. Hence, the image resolution and quality is more uniform for the whole field-of-view. The much smaller angular rotation of 360°/n also simplifies the gantry mechanics (cost reduction) and obviates the need to use expensive "slip-rings" which perform the double duties of rotation bearing and conduction of high-voltage and signals to/from the rotating detectors. For a 360°/n rotation, such electrical requirements may be performed, for example, by flexible ribbon cables 15, as shown in FIG. 2A. These flexible cables 15 may be similar to the use of flexible ribbon cables in the printing head of a computer ink-jet or dot matrix printer.

The present invention may therefore achieve low cost with less of a compromise in performance as compared to the prior art PET cameras. In fact, for imaging small organs (for example, head, neck, limb, breast, small animal models), this camera may perform better than even a full size, full ring, PET camera because of its much higher sensitivity, since the detectors are closer to the subject.

This low cost camera design may be used with any detector design. However, this camera design is advantageously mated to a detector design similar to that described in U.S. Pat. No. 5,319,204. That detector design, a quadrant-sharing-photomultiplier-detector, may lower detection system cost by 70% while maintaining the present state-of-art image resolution (4.5 mm), or it can be implemented to greatly improve imaging resolution (from 4.5 mm to 2.6 mm) while cutting detector cost by approximately 10%. However, this detector design requires a small detection gap between detector segments. A small rotation of the camera may be required to use this detector design. Thus, the rotating camera of the present invention facilitates the use of this detector design. Hence, combining the two designs, the present lower cost invention has a much higher image resolution than prior art cameras and a higher gamma-ray detection efficiency (translating to less a less noisy image or cleaner image) than the regular camera for small organ imaging.

Figure 4:
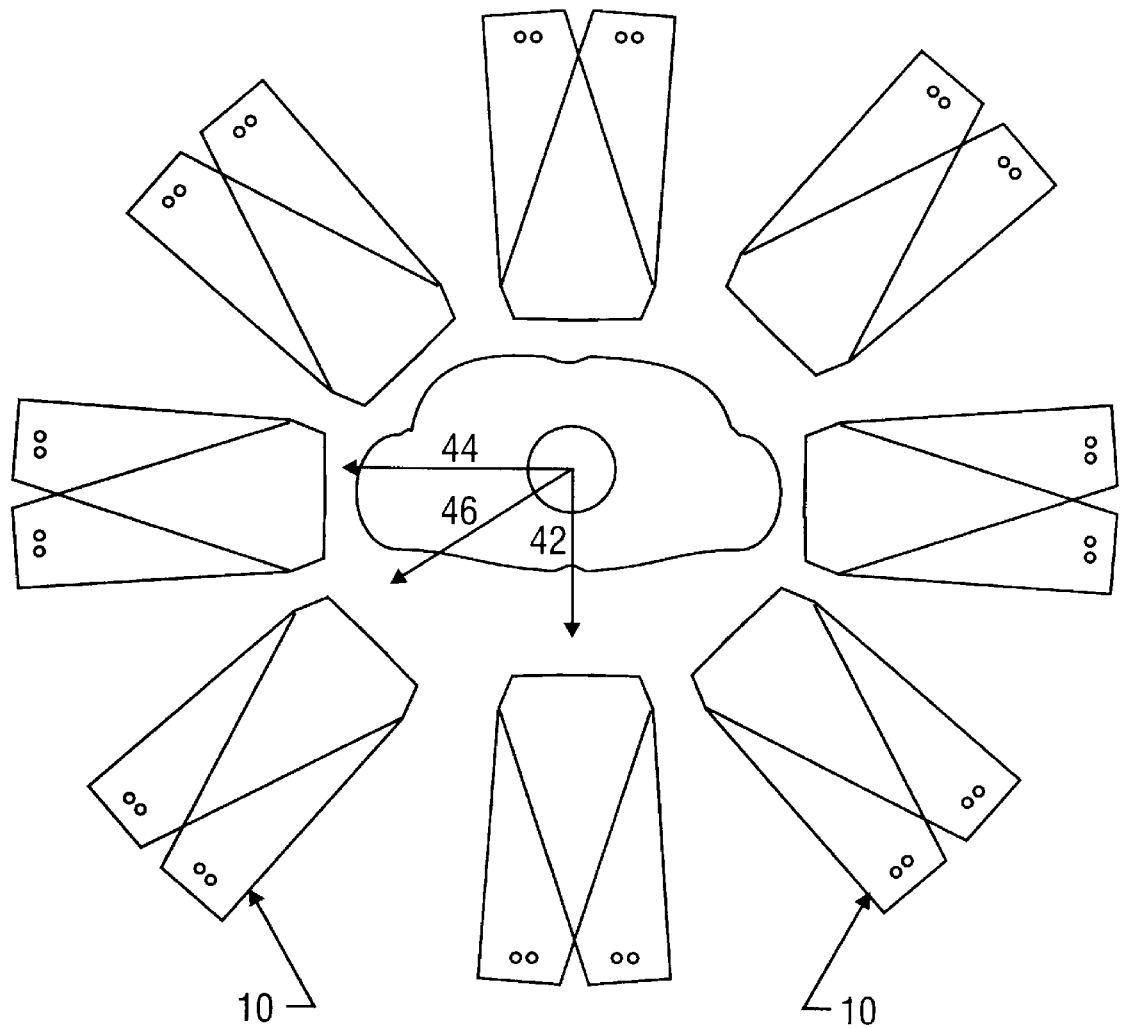
FIG. 4 is a diagram of the loci of one configuration of detector heads of a PET camera according to the present invention.

In an exemplary embodiment as shown in FIG. 4, each detector head 10 may be set to different radial positions from the center of the field-of-view (FOV) by sliding along, for example, a precision key-way on the gantry (not shown), with or without additional tilting of the detector heads 10 away from symmetric radial orientation and on the transaxial plane. The eight key-ways may be radially oriented. FIG. 4 shows an embodiment in which the top and bottom detector heads 10 are at the smallest radii 42, the two lateral detector heads 10 are at the largest radii 44 and the oblique detector heads 10 are at an intermediate radii 46. This configuration may be used to image an elliptical body cross-section. In a geometry in which the detector heads 10 are at their smallest diameter, the detector packing fraction equals that of a conventional camera with the added advantage of higher gamma capture efficiency, since sensitivity for the true events is inversely proportional to ring diameter. For imaging an adult body, the detector heads 10 may be retracted outward to a maximum diameter of approximately 70 cm to accommodate the large object. With this geometry, the detector packing fraction may be approximately 60%, which results in an approximate 40% decrease in detector components.

When the detector heads 10 are located at their maximum radial position, the detector ring formed by the heads may have eight large "detectorless" gaps. These "detectorless" gaps may leave sampling gaps in the sinogram if the camera heads remain in stationary angular positions. Therefore, in this large geometry mode, the camera may be rotated in steps as small as 0.5°–1° over an angular distance of up to approximately 45°, covering the sampling gaps in the sinogram. Sinograms (simulated) without rotation depicting these gaps are shown in FIG. 3A for the minimum ring diameter of 44 cm and in FIG. 3B for a larger ring diameter of 68 cm. From FIGS. 3A and 3B, it can be seen that the size of the gaps in the sinogram varies with the radial location of the camera heads. The small gaps in the 44 cm diameter mode may be eliminated by, for example, the backprojection-reprojection method, or by rotating the camera by a few degrees during imaging. The larger gaps in the larger diameter case may be eliminated by rotating the camera by up to 450° in small steps. To fill all the sinogram gaps like a solid detector ring, the correct rotation step size may be determined from the equation:

$$\Delta\theta = 2(\text{detector pitch})/D$$

where D is the detector diameter. For example, when D=70 cm, $\Delta\theta=0.45°$.

Figure 5:
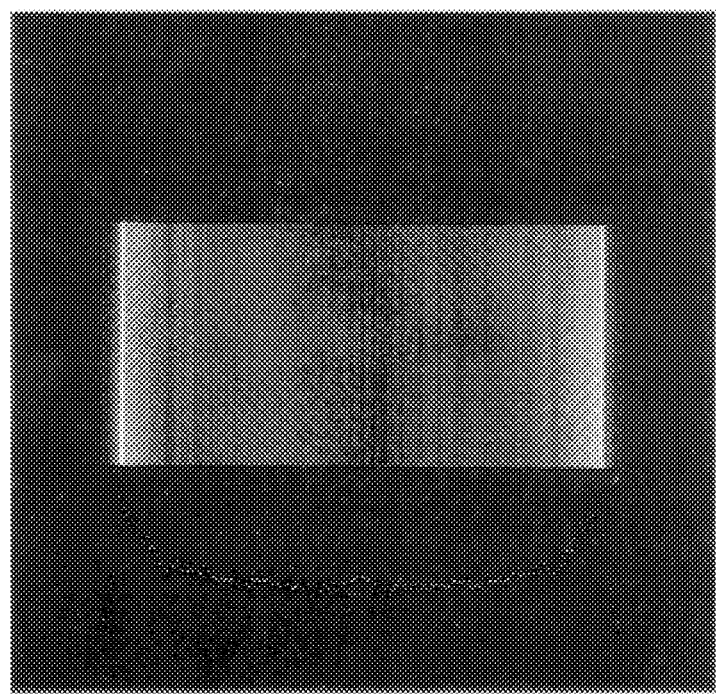
FIG. 5 is an illustration of a sinogram showing the data sampling of a PET camera according to the present invention having a small field-of-view and rotation and a curve showing the wavy pattern of sensitivity variation along the t-coordinate.
Figure 6:
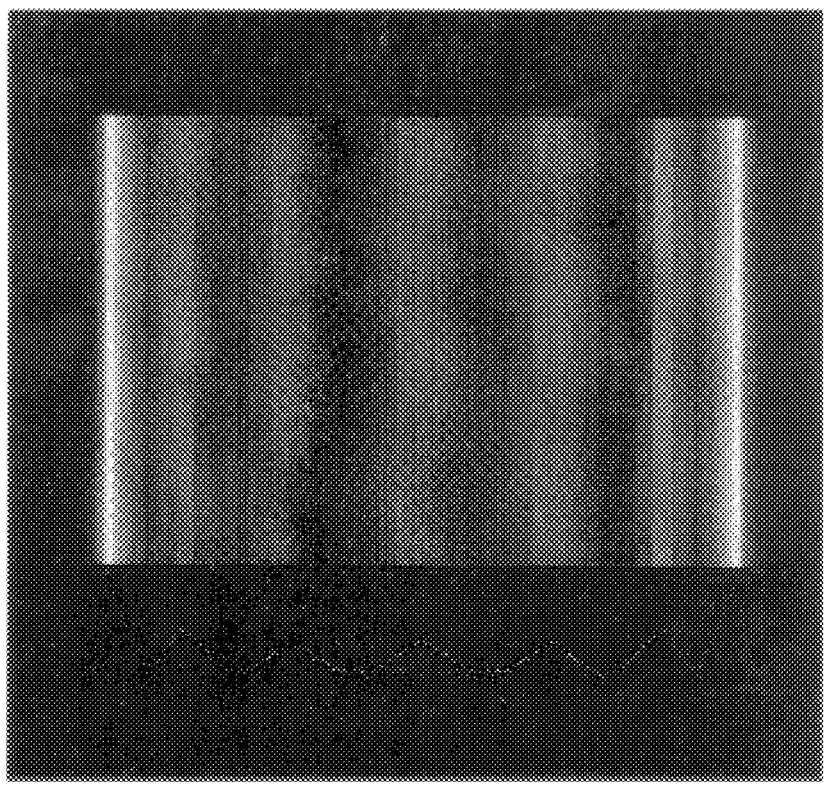
FIG. 6 is an illustration of a sinogram showing the data sampling of a PET camera according to the present invention having a larger field-of-view and rotation and a curve showing the wavy pattern of sensitivity variation along the t-coordinate.

FIGS. 5 and 6 are illustrations of sinograms showing the data sampling of a PET camera according to the present invention. FIGS. 5 and 6 are obtained by translating all of the "diamonds" in FIGS. 3A and 3B down by $\Delta\theta$ steps to 45° and summing over all of the steps, which is equivalent to the sampling effect of rotating the camera by $\Delta\theta$ steps to a total of 45°. Even with all the sinogram gaps filled, there may still be a variation of sampling sensitivity along the projection coordinate (t), as seen in FIGS. 5 and 6. Unlike a circular geometry, where each sinogram data bin is sampled by one detector coincidence pair with no sensitivity variations, the present invention uses a geometry in which each sinogram bin is sampled unequally by several detector pairs. This sensitivity variation along t is due to the difference in the number of times that each θ-t bin has been visited by detector pairs during the total 45° rotation.

With a larger gap (larger FOV), the t bins near the left/right edge points of the "diamonds" may be frequented much less by detector pairs than the t bins at the middle of the "diamonds," producing larger sensitivity differences. This sensitivity variation has a wavy pattern along the t-coordinate, as shown in the lower curves of FIGS. 5 and 6. This variation can be corrected by multiplying the image sinogram data with a function which is the inverse of this t-sensitivity variation function. The correction is dependent upon the radial positions of the detectors and the ratio of the arc subtended by the detectors and the detectorless gap. For the small diameter mode, the sensitivity variation is smaller, as shown in FIG. 6. The largest radial position of the detector is reached when the arc subtended by the detector inside the detector head 10 is approximately equal to the arc subtended by the detector gap. When this point is reached, no amount of rotation can prevent a data sampling gap from forming. Hence, in this invention, the ratio of the maximum detector ring diameter to the minimum detector ring diameter should be limited to 2:1 or less, when the camera is configured in a regular polygon geometry.

To restore some of the lost sensitivity for whole body imaging, one option may be to configure the camera into an irregular polygon; for example, to set the two lateral detector heads 10 at the largest separation (having a separation of between 40 cm and 60 cm), the top-bottom detector heads 10 at a smaller separation (having a separation of between 20 cm and 40 cm), and the four oblique detector heads 10 at an intermediate distance (having a separation of between 30 cm and 50 cm). With a 45° rotation, the loci of the detector heads 10 (with side shields) trace an elliptical patient opening for the adult body, as shown in FIG. 4. Since some of the detector heads 10 are closer to the body in this detector head arrangement, the detection sensitivity loss may be partly restored.

For breast imaging, the camera heads may be pushed into the smallest diameter with the gantry tilted horizontally, so that the patient is lying prone on top of the gantry, as shown in FIG. 2C. In this configuration, more breast tissue 8 is imaged and the sensitivity is an order of magnitude higher, because the large chest cross-section is not in the path of the gamma ray attenuating the signal and the detector ring comprising detector heads 10 is very close to the breast, increasing the solid-angle of detection.

To image metastases in the axillary lymph nodes, for example, the patient may be imaged supine inside the patient opening with the detector modules positioned at a large diameter (normal PET tomographic imaging). This transformable design allows for both high sensitivity tomographic imaging of the breast and important tomographic imaging of the axillary nodes (for cancer staging and treatment planning).

Figure 7:
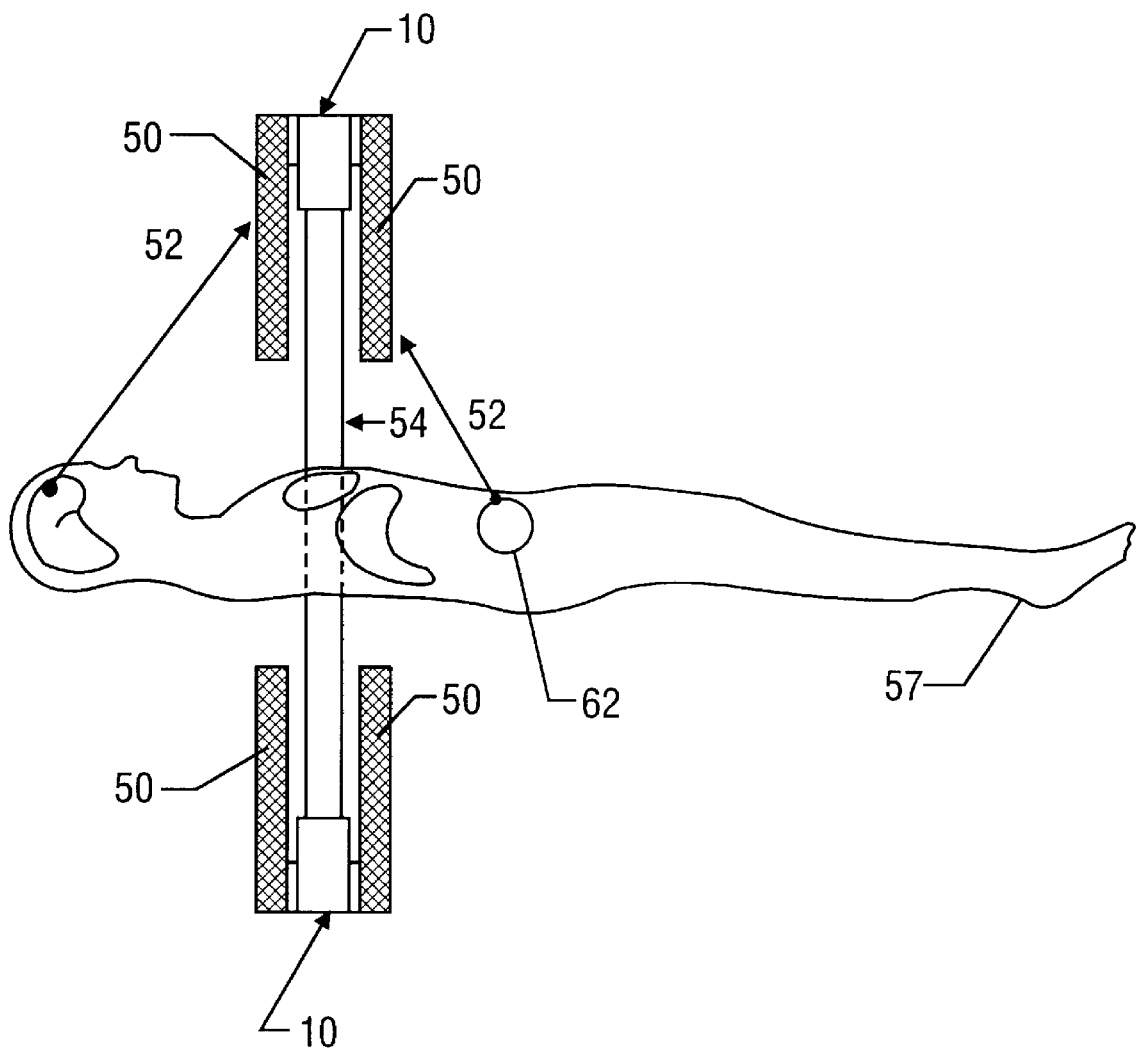
FIG. 7 is a cross-sectional view of a side-shield configuration of a prior art PET camera.
Figure 8:
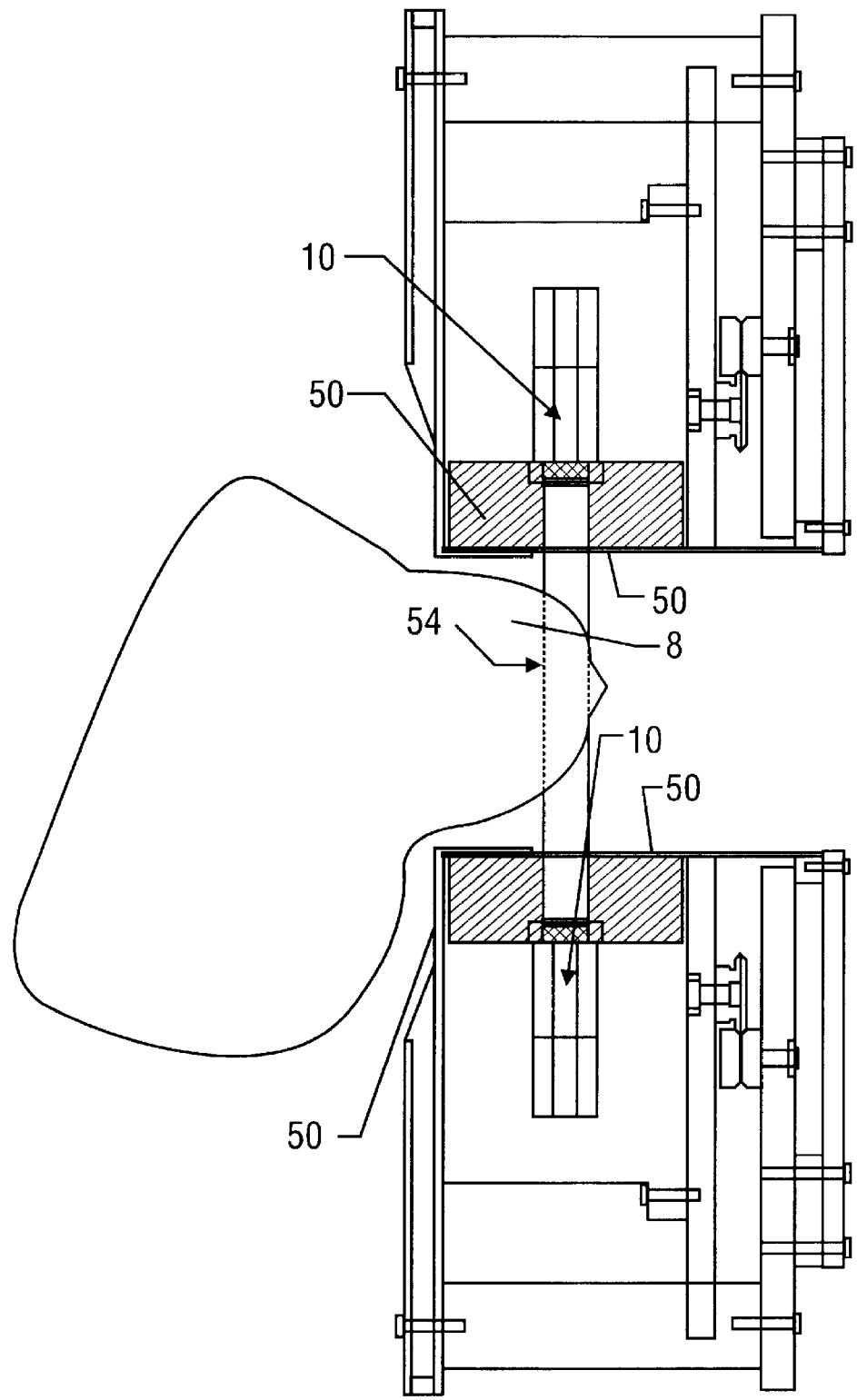
FIG. 8 is a cross-sectional view of a thick side-shield configuration of a prior art PET camera.

As illustrated in FIG. 7 for a prior art PET camera, shielding 50 is for blocking the gamma noise 52 coming from sections of the body 57 outside the coincidence field-of-view 54. However, for imaging the whole body, especially near the bladder region 62 (which traps a lot of water soluble radionuclide tracers), traditional cameras need very thick lead shielding (1"–2"). Since in the conventional design the shielding is fixed, the shielding must be thick enough for the worst case situation. If this thick shielding design is used for imaging the breast 8 in the mode shown in FIG. 8, a large part of the breast 8 will be missed by the camera, which is why conventional cameras do not image the breast in that manner (although this imaging configuration obviates the absorption of gamma-rays by the chest).

Figure 9:
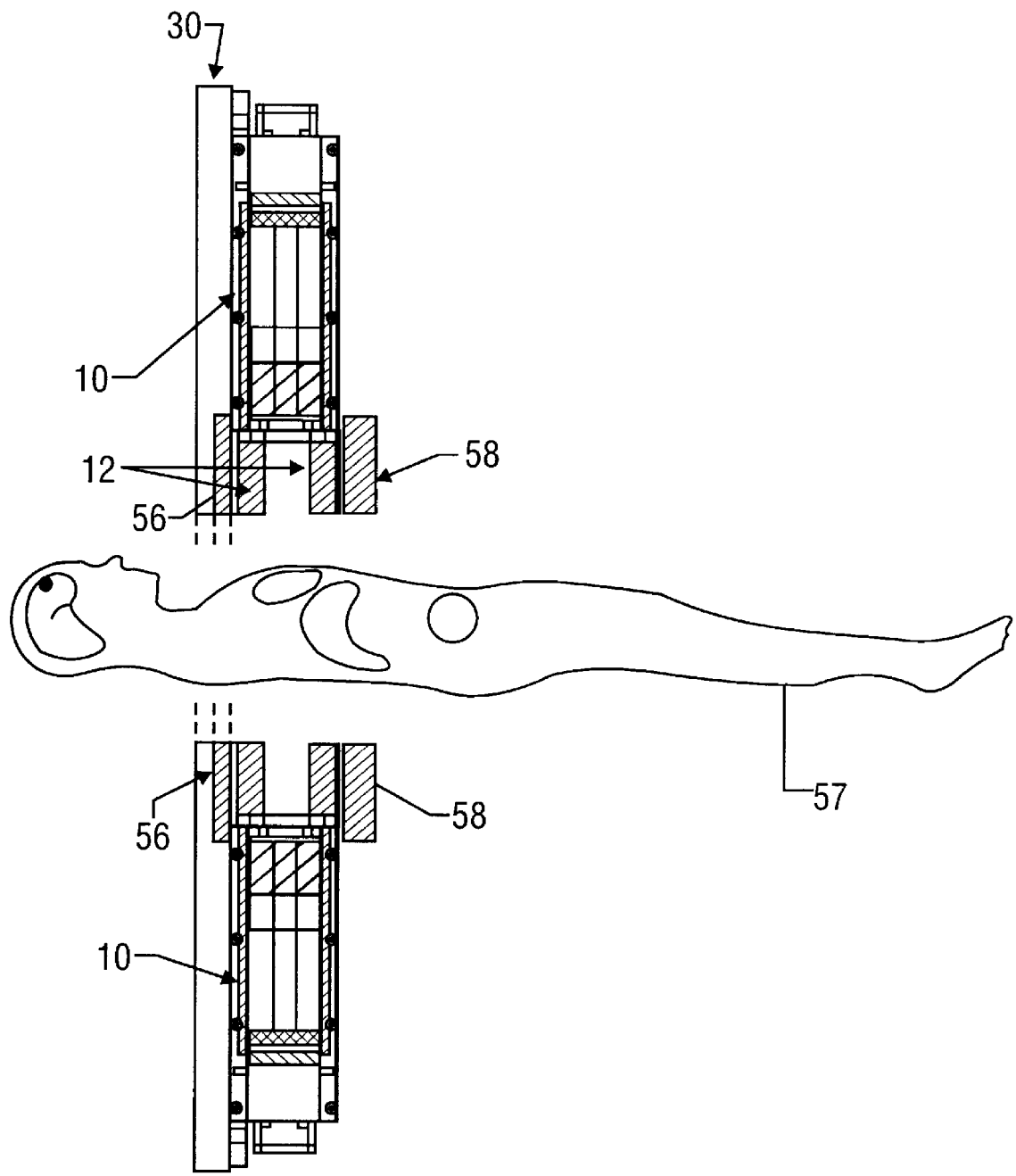
FIG. 9 is a cross-sectional view of a PET camera showing supplemental front and back shields for non-breast imaging according to the present invention.

To facilitate the convertible imaging mode, the lead-shielding system of the camera is also convertible. Specifically, the invention separates the shielding into several parts as shown in FIG. 9. As shown in FIG. 9, the detector head 10 carries part of the shield 12, which is thinner, for minimizing the missing of breast tissue. For imaging the body 57, there may be supplemental shielding 56 on the rotating plate 30 which holds the detector heads 10. As shown in FIG. 9, this shield 56 is fixed in place. Since this shield is opposite to the breast in the breast imaging mode (not shown), it does not affect the breast imaging mode. However, in the body imaging mode, it can effectively shield the body radiation. For more effective shielding, this fixed shield 56 may be mounted on the rotating plate 30 instead of the fixed plate 35, so that the supplemental shielding 56 is in intimate contact with the detector head 10. In the rotating camera of the prior art, this shield is on the fixed portion of the gantry.

There may be another piece of supplemental shield on the "front" side in the whole body mode as shown in FIG. 9. This "front" supplemental shield 58 can either be hung from the fixed plate 35, as in FIG. 9, or it can be free standing. This front supplemental shield 58 may be removed when imaging a breast. For imaging a brain with the detector heads 10 in the small diameter position, the body-front-supplemental shield 58 may be replaced by a small diameter front supplemental shield (not shown). In brain imaging, the back-supplemental-shield 56 (for body) has no shielding effect since the detector heads 10 are at a different diameter from the back shield, but this is not important because the entire body 57 is on the front side of the gantry and the limited amount of shield 12 carried by the detector heads 10 is sufficient to shield the small amount of stray scatter radiation from the back side.

Figure 10:
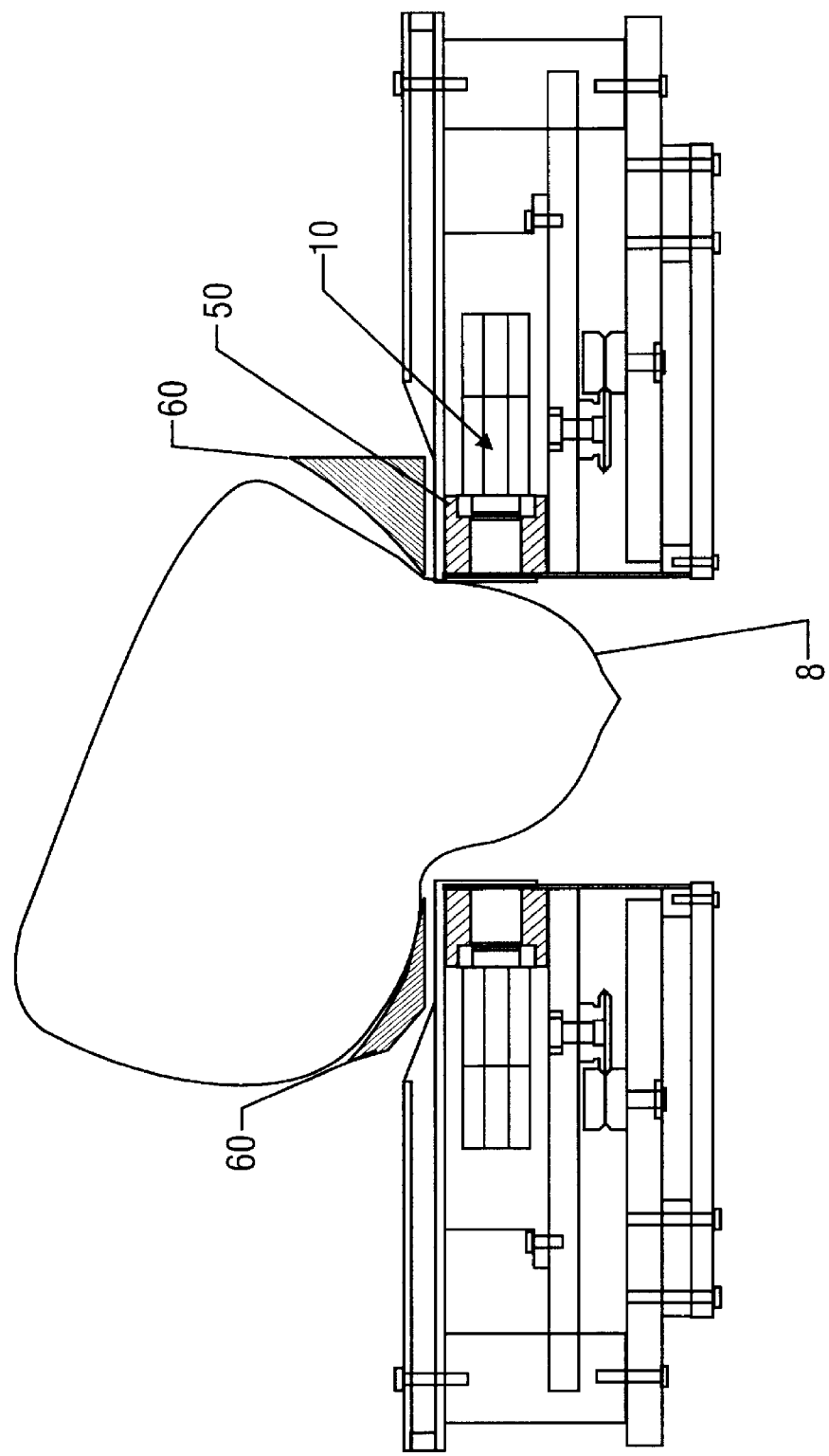
FIG. 10 is a cross-sectional view of a PET camera showing additional customized body-contoured shields for breast imaging without missing breast tissue according to the present invention.

For imaging the breast, another body-contoured front-supplemental-shield 60 may be hung from the camera as shown in FIG. 10, to supplement the detector-head shield without decreasing the amount of image-able breast tissue 8. This fragmental shielding system (dividing the shield into several parts) optimizes the shielding and imaging more efficiently for different organs.

The present shielding system has several advantages. Part of the shield system is carried by the detector heads 10, which move, while the supplemental shields 56 are mounted away from the detector heads 10. Further, the front supplemental plate 58 is exchangeable depending on the object being imaged.

Figure 11:
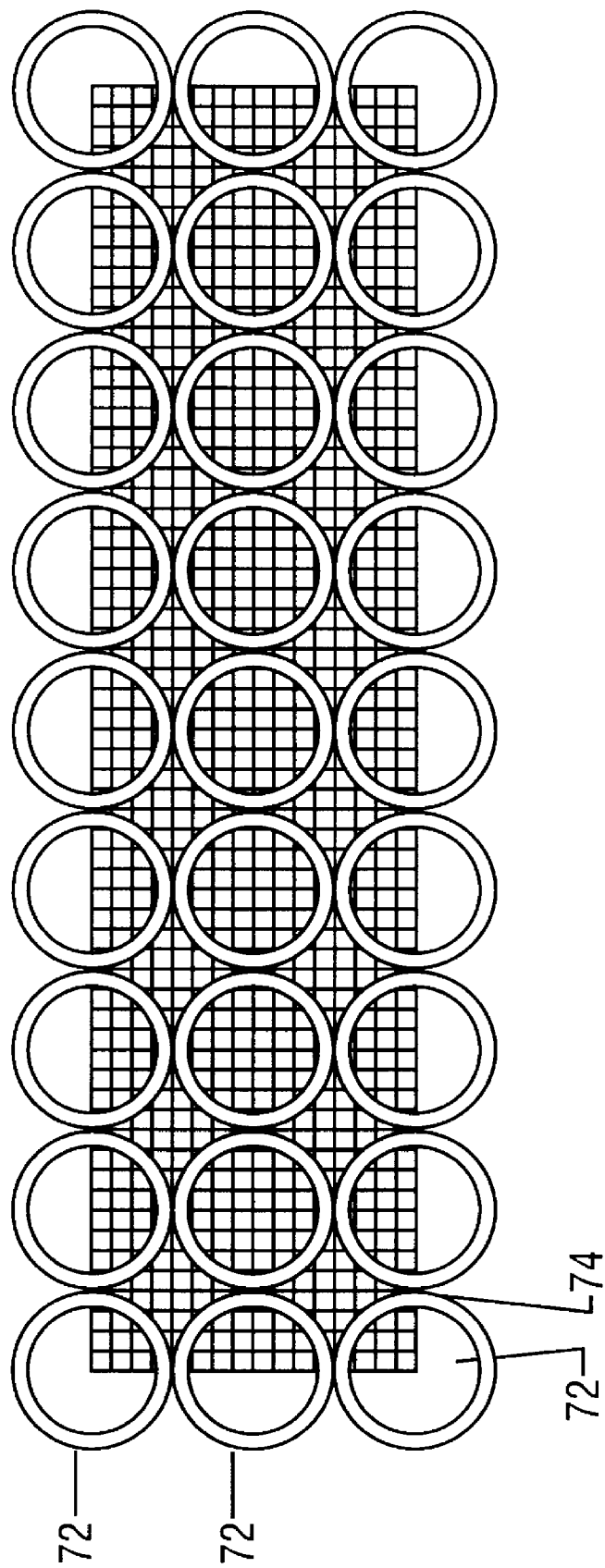
FIG. 11 is a diagram of a detector configuration used in the present invention.
Figure 12:
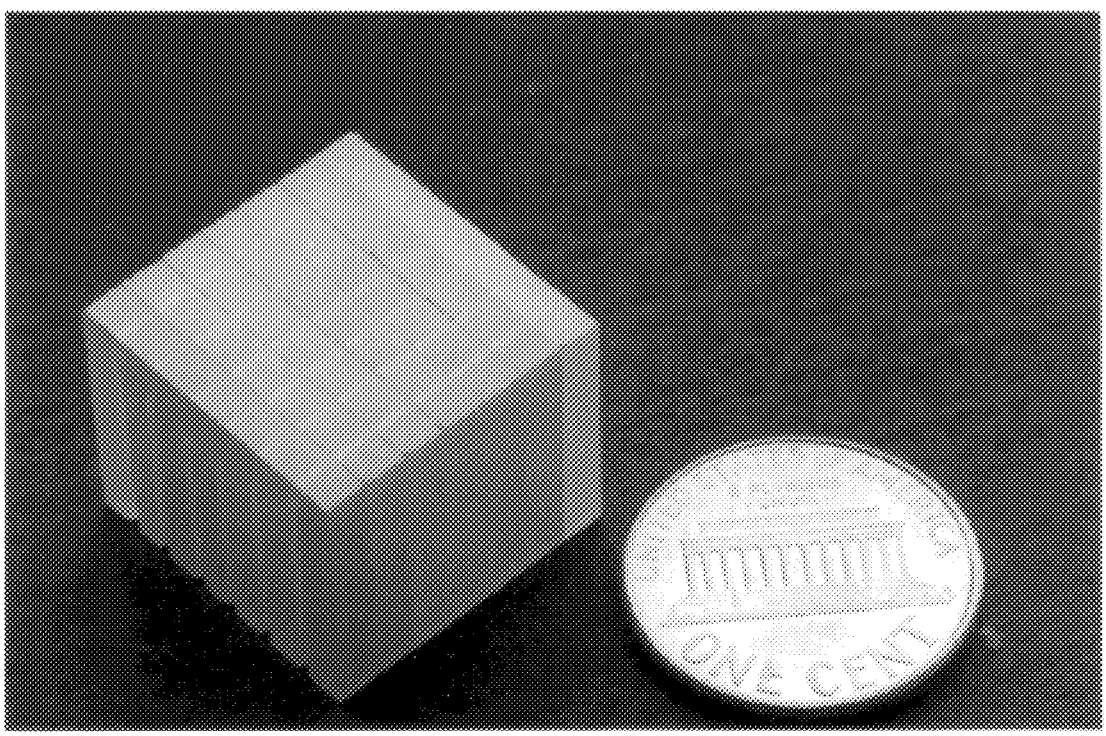
FIG. 12 is an illustration of a scintillation crystal block used in the present invention.
Figure 13:
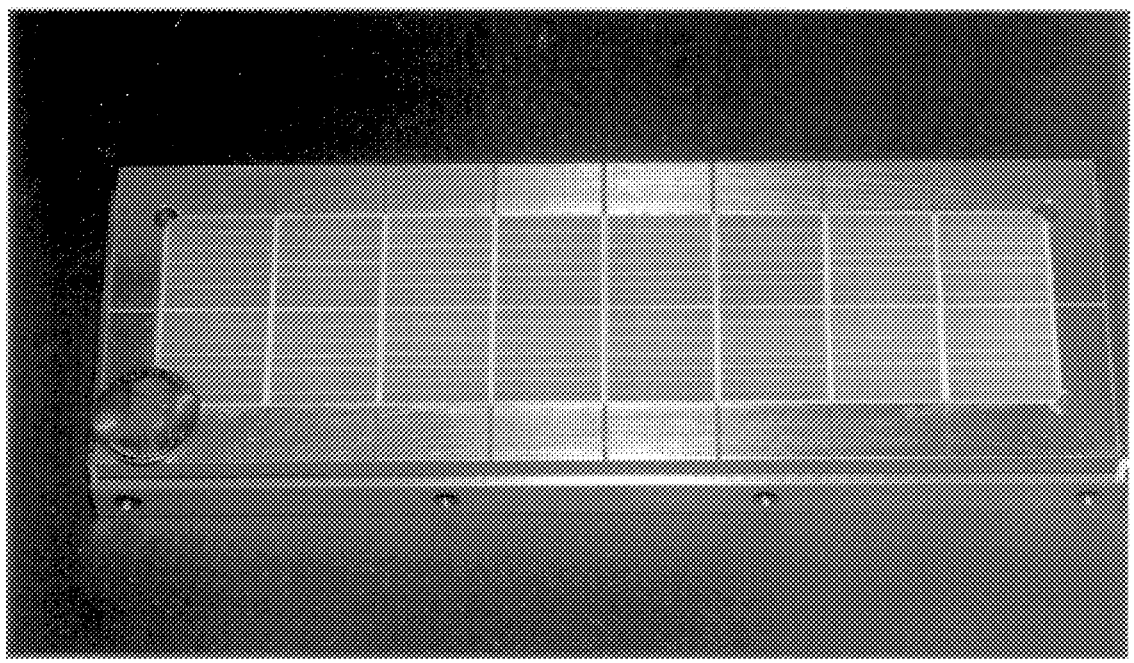
FIG. 13 is an illustration of a block array of scintillation crystals for use in a detector head of the present invention.

A quadrant-sharing PMT design, as shown in FIG. 11, may be adopted for a camera according to the present invention. An example of such a design is disclosed in U.S. Pat. No. 5,453,623, which is hereby incorporated by reference. In this design, a plurality of circular PMT's 72 are placed adjacent to each other, such that each of a plurality of crystal arrays or detector blocks 74 is directly adjacent and optically coupled to four adjacent quadrants of four adjacent PMT's 72. This design improves detector spatial resolution while lowering the cost of the PMT's with the use of larger and less expensive circular PMT's, for example, 19 mm PMT's. The BGO scintillation detector blocks 74 may be close-packed into a BGO bed. The block size may be, for example, 19×19 mm with a BGO crystal pitch size of 2.7×2.7 mm. The crystals may be glued together in one dimension (transaxial) with a very small glue-paint-gap of 0.07 mm, which provides a packing fraction of approximately 97% transaxially. This high packing fraction partially compensates for the sensitivity loss due to the gaps between detector segments. The other dimension may be saw-cut, for example. A detector block of the present invention with 49 BGO elements is shown in FIG. 12 (with a penny shown to illustrate relative size). FIG. 13 shows a block array of scintillation crystals for use in a detector head of the present invention (with a penny shown to illustrate relative size).

Figure 14:
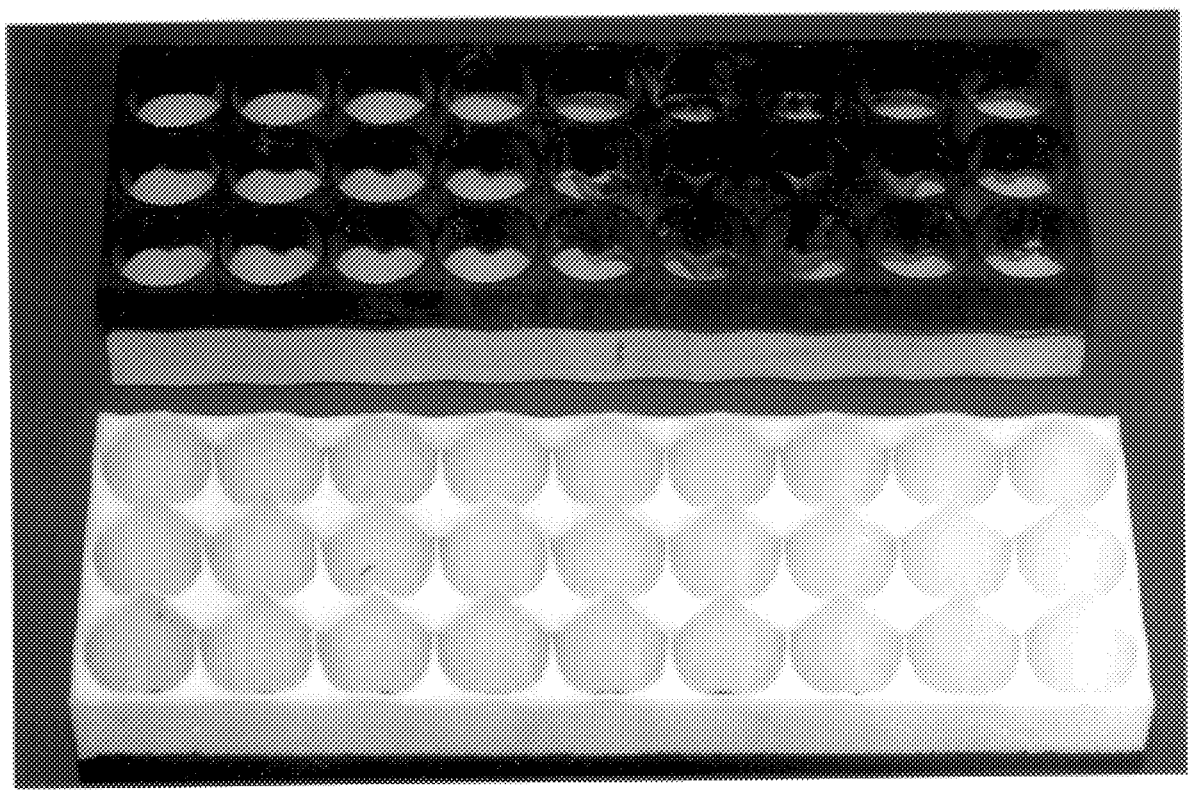
FIG. 14 is an illustration of a honey comb matrix (plastic cast) for supporting and positioning the PMT inside the detector head.

Inside the detector heads 10 there may be, for example, a honey-comb structural matrix (plastic cast) having holes large enough to accommodate a PMT to fix the PMT locations for ease and accuracy of PMT positioning. FIG. 14 shows the honeycomb cast 76 from the side adjacent to the PMT's and voltage dividers (top figure) and from the side adjacent to the BGO crystal arrays (bottom figure). Some of the holes may be slightly larger than the average PMT size so that a PMT constructed off-tolerance will fit within the hole. The ease of positioning aids in both PMT assembly and replacement processes. This plastic cast, as shown in FIG. 14, may also have, for example, a matrix of concave light reflecting surfaces 82 to recapture the light which would have been lost in the large gaps between each group of 4 circular PMT's. The cast may be white on the reflecting surface side 76A. The whiteness may be painted on, or may be the original color of the cast for this light reflection purpose.

Figure 15A:
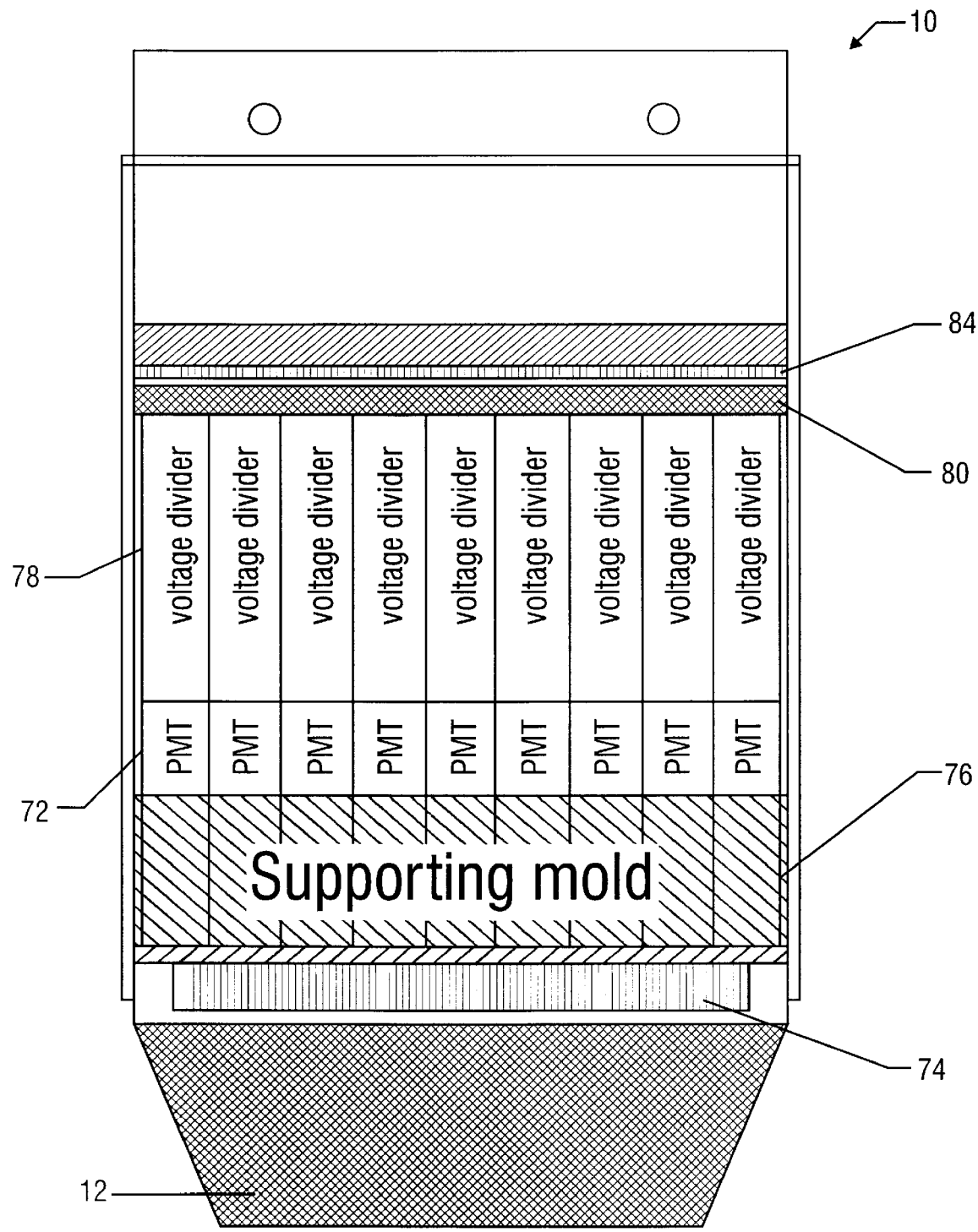
FIG. 15A is a block diagram of a detector head of the present invention.
Figure 15B:
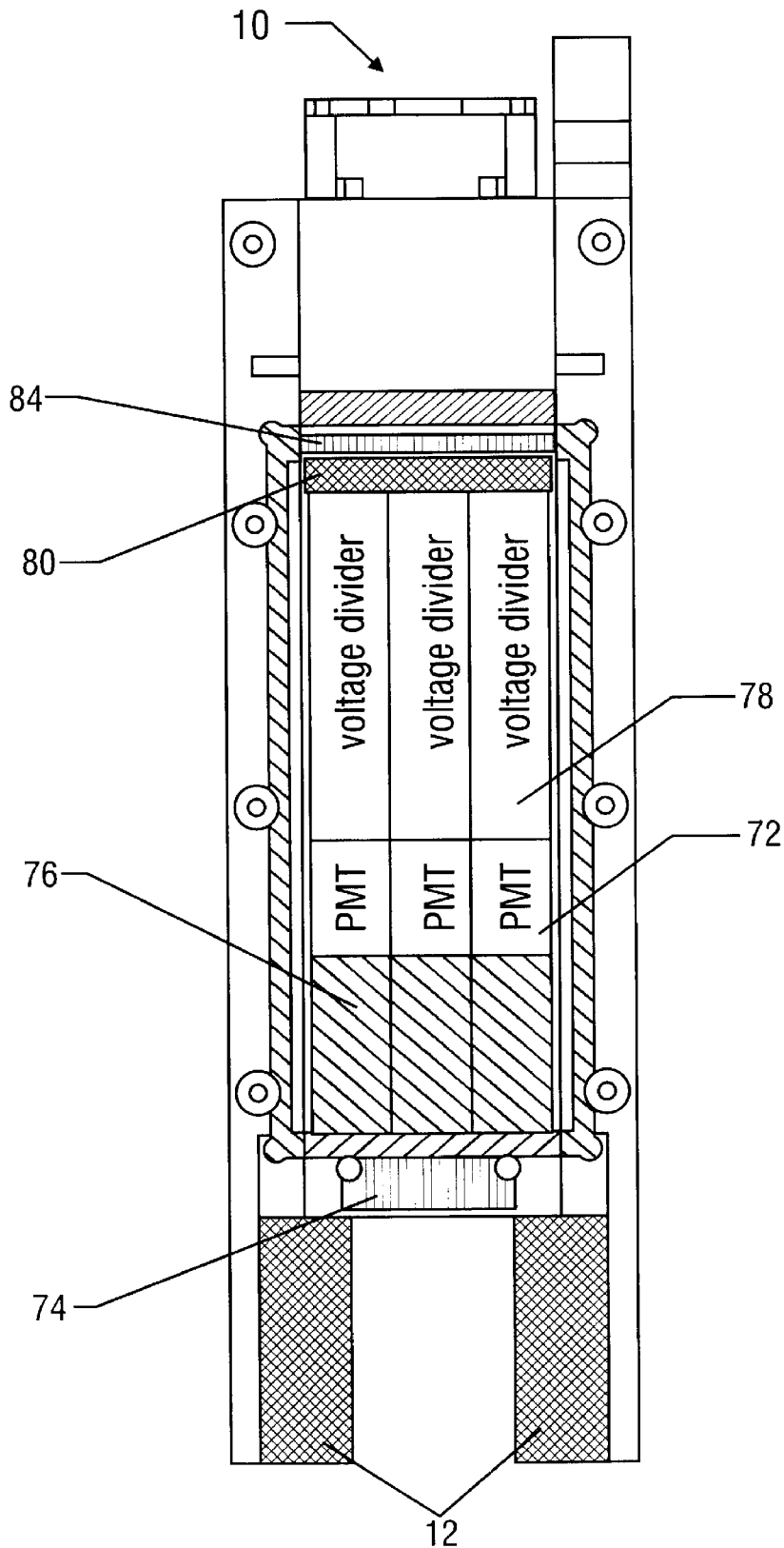
FIG. 15B is a cross-sectional view of the detector head of FIG. 15A.

A detector head configuration as used in the present invention is shown in FIGS. 15A and 15B. Detector head 10 includes a plurality of BGO crystals or detector blocks 74 to which are connected a plurality of PMT's 72 through the honeycomb matrix cast 76. The PMT's 72 are connected to a plurality of voltage dividers 78, held in place by a PMT compression and seal 80 and compression plate 84. As seen in FIG. 15B, the BGO crystals 74 may be shielded on both sides by side shields 12, which may be comprised of lead/uranium. These side shields 12 facilitate breast imaging as shown in FIG. 2C; the normally used thick lead side shields (1"–2") of prior art PET cameras are too thick, and leave a portion of the breast tissue outside the field-of-view of the camera.

The present invention may therefore reduce the detector components and associated front-end electronics required for a conventional PET camera by approximately 40–50%, which can lower the production cost of the PET camera. Coupling to a lower cost, higher resolution detector designs (such as U.S. Pat. Nos. 5,319,204 and 5,453,623, which are hereby incorporated by reference), the present invention has an even lower production cost and higher image resolution (2.7–3 mm) than existing PET cameras.

It is to be noted that the present invention may also be used to develop an even lower cost camera than the camera described above. For this embodiment, the detector pitch size may be increased to that of the conventional high resolution cameras (4–5 mm). With this detector size, the PMT cost (typically 50% of the production cost) may be further reduced by approximately 60% using the same quadrant-sharing PMT design. Adding this PMT cost reduction to the approximately 40–50% reduction in detection-component cost from the variable field camera concept, the production cost of the camera may be reduced substantially. For imaging brains, breasts, limbs and animal models, this larger detector implementation would yield the same image resolution and higher detection sensitivity. For imaging adult bodies, the larger detector gaps will lower the detection sensitivity compared to the conventional camera.

The apparatus and methods disclosed and claimed herein can be made and executed without undue experimentation in light of the present disclosure. While the apparatus and methods of this invention have been described in terms of exemplary embodiments, it will be apparent to those of skill in the art that variations may be applied to the apparatus, methods and in the steps or in the sequence of steps of the method described herein without departing from the concept, spirit and scope of the invention. All substitutes and modifications apparent to those skilled in the art are deemed to be within the spirit, scope and concept of the invention as defined by the appended claims.

What is claimed is:

1. A PET camera for imaging an object, the camera comprising:

a plurality of position sensitive radiation detectors capable of radial translation with respect to a central axis, said plurality of position sensitive radiation detectors arranged in arcuate relation to each other and adapted to surround said object to be imaged.

2. The PET camera as claimed in claim 1, wherein each of said plurality of position sensitive radiation detectors comprise a plurality of photodetectors and a plurality of arrays of scintillation crystals, said plurality of photodetectors positioned adjacent said plurality of arrays of scintillation crystals.

3. The PET camera as claimed in claim 2, wherein said photodetectors comprise photomultiplier tubes.

4. The PET camera as claimed in claim 3, wherein at least one of said photomultiplier tubes is adjacent one quadrant of each of four adjacent arrays of scintillation crystals.

5. The PET camera as claimed in claim 1, wherein said plurality of position sensitive radiation detectors comprise at least four detectors.

6. The PET camera as claimed in claim 3, wherein a honeycomb matrix is adapted within each of said plurality of position sensitive radiation detectors to support said photo-multiplier tubes.

7. The PET camera as claimed in claim 6, wherein said honeycomb matrix further comprises a matrix of concave light-reflecting surfaces.

8. The PET camera as claimed in claim 1, wherein at least two of said plurality of position sensitive radiation detectors are at different radial positions relative to each other with respect to said central axis.

9. The PET camera as claimed in claim 1, wherein said plurality of position sensitive radiation detectors are mounted on a gantry.

10. The PET camera as claimed in claim 9, wherein said gantry comprises a rotatable platform.

11. The PET camera as claimed in claim 10, wherein said rotatable platform is capable of 360°/n rotation, where n is the number of said position sensitive radiation detectors surrounding said object.

12. The PET camera as claimed in claim 1, wherein each of said plurality of position sensitive radiation detectors further comprises a pair of gamma-ray shields.

13. The PET camera as claimed in claim 12, further comprising a plurality of supplementary gamma-ray shields positioned to surround said plurality of position sensitive radiation detectors.

14. The PET camera as claimed in claim 1, wherein a ratio of a maximum diameter of a ring created by said plurality of position sensitive radiation detectors to a minimum diameter of a ring created by said plurality of position sensitive radiation detectors is not greater than 2:1.

15. The PET camera as claimed in claim 1, further comprising a cyclical sensitivity-variation correction system, said correction system being dependent on radial positions of two of said plurality of position sensitive radiation detectors and a ratio of an arc subtended by said two of said plurality of position sensitive radiation detectors and a detectorless gap between said two of said position sensitive radiation detectors.

16. A method of testing a patient for breast cancer, comprising the steps of:

obtaining a PET imaging apparatus having a plurality of position sensitive radiation detectors capable of radial translation with respect to a central axis, said plurality of position sensitive radiation detectors arranged in arcuate relation to each other and adapted to surround said patient;

placing a gantry containing said imaging apparatus in a horizontal or tilted position;

injecting said patient with radioactive isotopes;

positioning said patient in a substantially prostrate orientation, thereby placing a breast of said patient adjacent said plurality of position sensitive radiation detectors;

adjusting said plurality of position sensitive radiation detectors, thereby placing said plurality of position sensitive radiation detectors within close proximity to said breast; and imaging said breast using said plurality of position sensitive radiation detectors.

17. A method of imaging an object using a PET camera, comprising the steps of:

obtaining a PET imaging camera having a plurality of position sensitive radiation detectors capable of radial translation with respect to a central axis, said plurality of position sensitive radiation detectors arranged in arcuate relation to each other and adapted to surround said object; said plurality of position sensitive radiation detectors including top, bottom, side and oblique detectors, said top and bottom detectors opposing each other, said side detectors opposing each other and said oblique detectors opposing each other;

placing said object adjacent said plurality of detectors;

adjusting said plurality of position sensitive radiation detectors such that said side detectors have a greatest separation, said top and bottom detectors have a least separation, said oblique detectors have a separation intermediate said greatest separation and said least separation, such that said plurality of position sensitive radiation detectors form an elliptical arrangement about said object; and imaging said object using said plurality of position sensitive radiation detectors.

* * * * *